(12) United States Patent
Davison et al.

(10) Patent No.: US 10,772,578 B1
(45) Date of Patent: Sep. 15, 2020

(54) LARGE DIAMETER ROTARY MOTOR DRIVEN BY FLUX-SWITCHING

(71) Applicant: KOLLMORGEN CORPORATION, Radford, VA (US)

(72) Inventors: James Davison, Blacksburg, VA (US); Jerry Brown, Radford, VA (US)

(73) Assignee: KOLLMORGEN CORPORATION, Radford, VA (US)

( * ) Notice: Subject to any disclaimer, the term of this patent is extended or adjusted under 35 U.S.C. 154(b) by 202 days.

(21) Appl. No.: 15/154,853

(22) Filed: May 13, 2016

Related U.S. Application Data

(60) Provisional application No. 62/162,620, filed on May 15, 2015.

(51) Int. Cl.
| | |
|---|---|
| *H02K 1/17* | (2006.01) |
| *H02K 7/08* | (2006.01) |
| *H02K 1/14* | (2006.01) |
| *A61B 6/03* | (2006.01) |
| *H02K 1/27* | (2006.01) |
| *H02K 1/16* | (2006.01) |
| *A61B 6/04* | (2006.01) |

(52) U.S. Cl.
CPC ............... *A61B 6/035* (2013.01); *A61B 6/04* (2013.01); *H02K 1/148* (2013.01); *H02K 1/16* (2013.01); *H02K 1/17* (2013.01); *H02K 1/27* (2013.01); *H02K 7/08* (2013.01)

(58) Field of Classification Search
CPC .......... H02K 1/17; H02K 21/38; H02K 21/40; H02K 21/42; H02K 21/44

USPC .............................................. 310/181, 154.02
See application file for complete search history.

(56) References Cited

U.S. PATENT DOCUMENTS

| | | | | |
|---|---|---|---|---|
| 3,689,787 | A  * |  9/1972 | Saretzky | H02K 37/20 310/266 |
| 2009/0160391 | A1* |  6/2009 | Flynn | H02K 19/103 318/701 |
| 2010/0123426 | A1* |  5/2010 | Nashiki | H02K 1/12 318/701 |
| 2010/0314962 | A1* | 12/2010 | Shiga | H02K 1/143 310/156.01 |

(Continued)

OTHER PUBLICATIONS

"Integral, adj. and n." OED Online. Oxford University Press, Jun. 2018. Web. Jul. 21, 2018.*

(Continued)

*Primary Examiner* — Thomas Truong
(74) *Attorney, Agent, or Firm* — Day Pitney LLP

(57) ABSTRACT

A rotary motor comprising an annular rotatable bearing having an inner surface having a diameter equal to or greater than 0.5 meters and an outer surface, the bearing including a plurality of magnetic rotor teeth elements positioned around a circumference of the outer surface and a stator including a plurality of permanent magnets and a plurality of energizable coils, the stator mounted separately from and positioned with respect to the bearing such that the plurality of rotor teeth elements of the bearing are radially proximate to the permanent magnets of the stator. Upon application of alternating current in a flux switch pattern in the plurality of energizable coils of the stator, torque is applied to the plurality of magnetic rotor teeth elements.

4 Claims, 7 Drawing Sheets

(56) References Cited

U.S. PATENT DOCUMENTS

2013/0049372 A1* 2/2013 Lagerweij ............... F16C 19/54
290/55

OTHER PUBLICATIONS

Ditmanson et al, "A New Modular Flux-Switching Permanent Magnet Drive for Large Wind Turbines", IEEE, pp. 896-903, 2013.
Ditmanson et al, "A Prototype 3.2 MW Flux-Switching Permanent Magnet Drive for Large Wind Turbines", IEEE, pp. 956-963, 2018.

* cited by examiner

US 10,772,578 B1

LARGE DIAMETER ROTARY MOTOR DRIVEN BY FLUX-SWITCHING

CLAIM TO PRIORITY

This patent application claims the benefit of priority to U.S. Provisional Patent Application Ser. No. 62/162,620, filed May 15, 2015. This Provisional patent application is incorporated by reference herein in its entirety for any purpose whatsoever.

FIELD OF THE INVENTION

The present invention relates generally to permanent magnet electric motors and, more particularly, to a large diameter rotary motor bearing driven by a flux-switch motor topology.

BACKGROUND OF THE INVENTION

Flux-switch motor topologies employ a stator having permanent magnets and coils through which alternating current is applied, and an interior rotor composed of or including magnetically permeable material. When alternating current is applied to the coils of the stator, the variation in magnetic flux in the stator generates a torque on the rotor.

In large direct drive applications, because of the relatively high cost of magnets and mounting provisions for them, there is an interest in minimizing the amount of magnetic material being used in construction of the motor as well as how the magnets are mounted. In certain applications, even though the motion requirements in terms of torque or power may not demand it, particularly with regard to large permanent magnet motors, the geometry of the motor itself requires that the magnetic materials subtend the entire 360 degrees of rotation, resulting in the use of greater volumes of permanent magnets than necessary and requiring costly mounting provisions. This leads to increased cost, weight and complexity of the motor device.

SUMMARY OF THE INVENTION

The present invention provides a rotary motor comprising an annular rotatable bearing having an inner surface having a diameter equal to or greater than 0.5 meters and an outer surface, the bearing including a plurality of magnetic rotor teeth elements positioned around a circumference of the outer surface and a stator including a plurality of permanent magnets and a plurality of energizable coils, the stator mounted separately from and positioned with respect to the bearing such that the plurality of rotor teeth elements of the bearing are radially proximate to the permanent magnets of the stator. Upon application of alternating current in a flux switch pattern in the plurality of energizable coils of the stator, torque is applied to the plurality of magnetic rotor teeth elements.

The present invention also provides a Computed Tomography scanner comprising a platform for receiving and supporting a patient, a rotary motor and including an annular rotatable bearing, and a radiation source coupled to the rotatable bearing. The rotatable bearing having an inner surface enclosing an inner space in which the platform may be received, the inner surface having a diameter of 0.5 m or greater, and an outer surface including a plurality of magnetic rotor teeth. The rotary motor further includes a stator mounted separately from and positioned with respect to the bearing such that the plurality of rotor teeth elements of the bearing are radially proximate to the permanent magnets of the stator, the stator including a plurality of permanent magnets and a plurality of energizable coils wherein upon application of alternating current in a flux switch pattern in the plurality of energizable coils of the stator, torque is applied to the plurality of magnetic rotor teeth elements.

DETAILED DESCRIPTION

Figure 5:
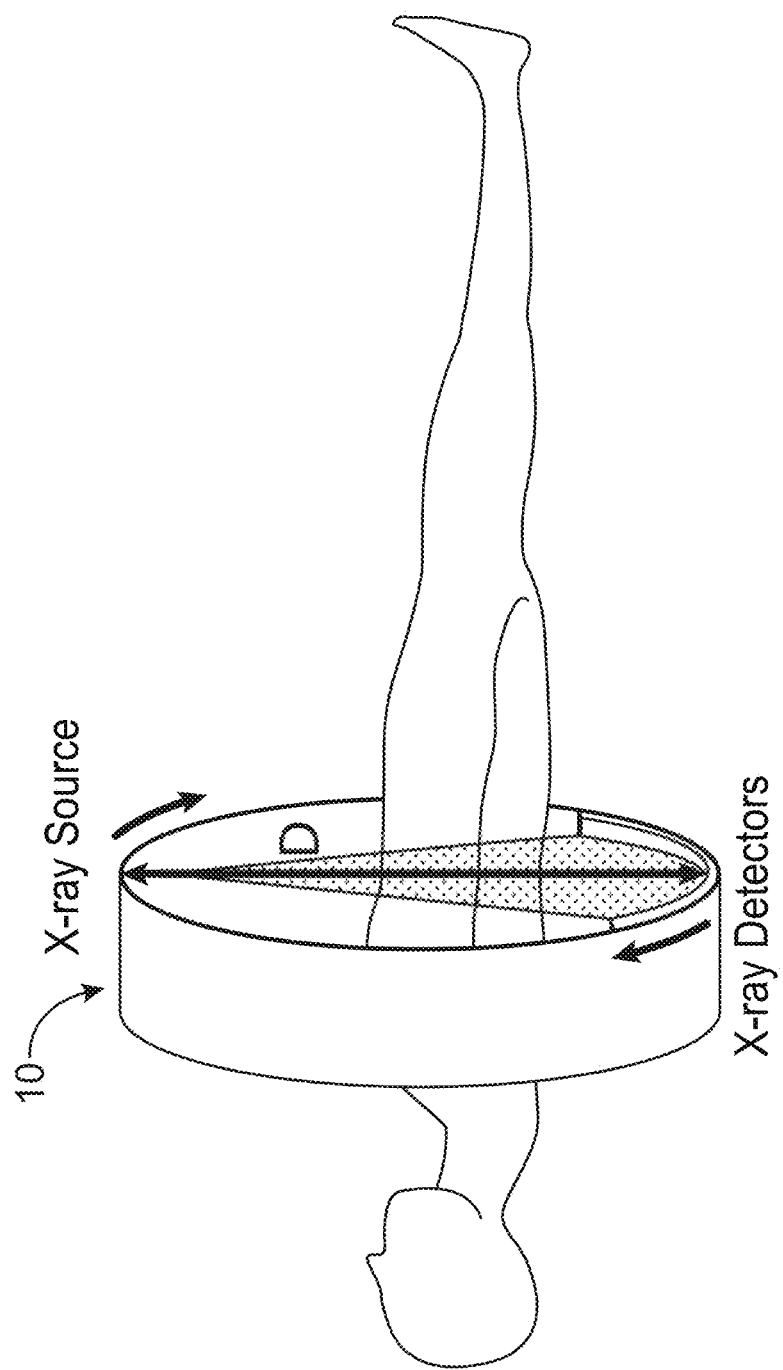
FIG. 5 is a schematic diagram of a patient in a computer-aided tomography (CT) scanner.

There are a number of applications in which a mechanical assembly is rotated around a large inner space having, such as Computed Tomography scanning (CT scanning). FIG. 5 is a schematic illustration showing a patient being examined in a CT scanner. In a CT scan procedure, the patient lies flat on a platform, and the platform slides into a tunnel containing the scanning equipment, for example a radiation source 10, which is made to rotate along a circular track of diameter (D) around the patient. The diameter (D) is sufficient to clear the full shoulder-to-shoulder width of a patient with adequate clearance. In some embodiments the radiation source may be coupled to an annular bearing, which is rotated by a motor (not shown).

The present invention provides a low-cost rotary motor especially suited for such applications in which a flux-switch rotor can be manufactured as an integral part of the bearing annulus, and the stator can have a reduced-arc length (i.e., subtend less than 360 degrees around the rotor). The reduction of the circumferential length of the stator is particularly advantageous in large diameter motor applications as the reduction in the amount of magnetic material used in the stator is particularly significant.

Figure 1:
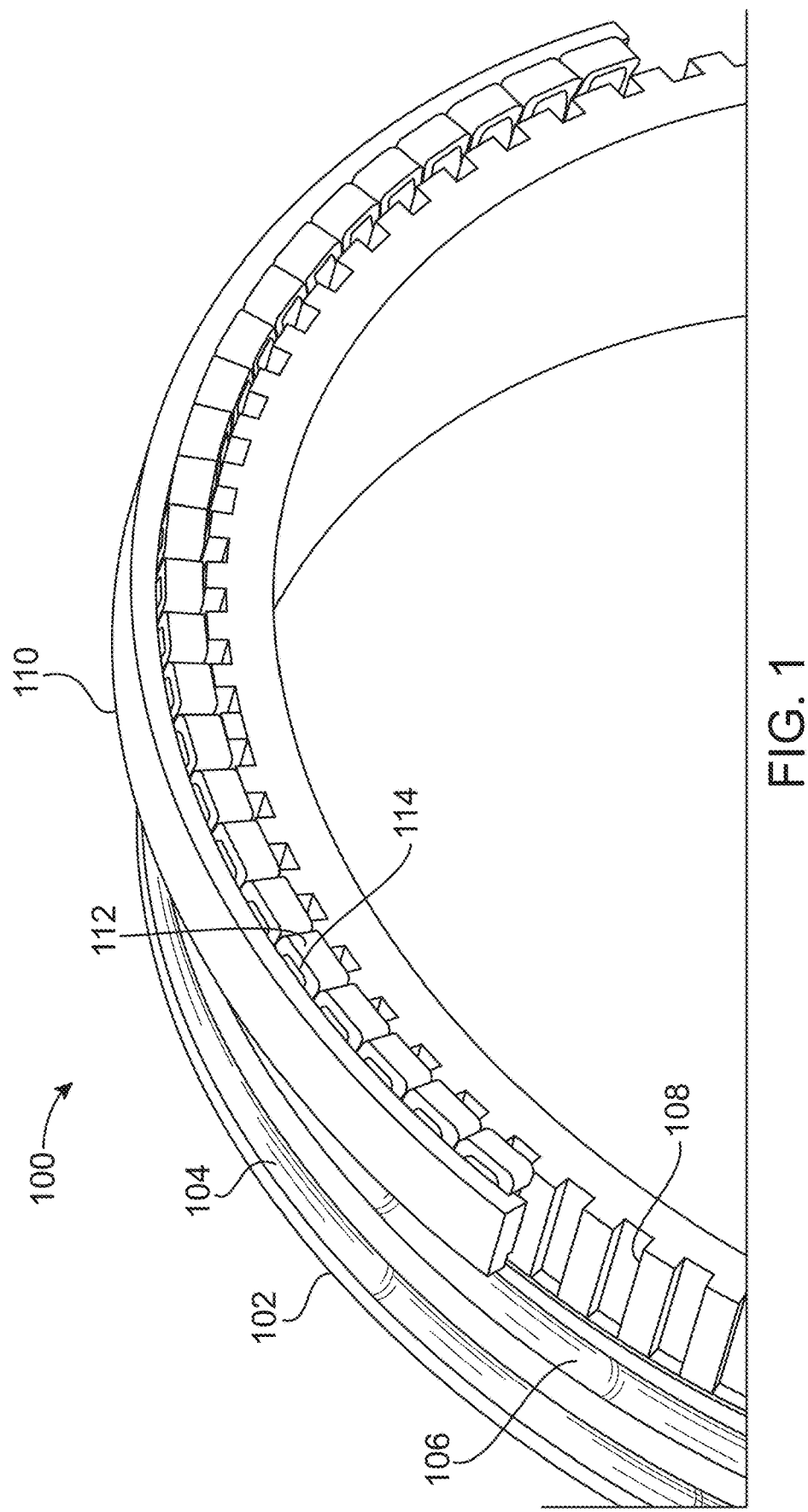
FIG. 1 is a perspective view of a section of a rotary motor according to an exemplary embodiment of the present invention.

FIG. 1 is a perspective view of a portion of the rotary motor 100 using a flux-switch topology according to an embodiment of the present invention. The rotary motor 100 includes an annular rotor bearing 100 ('rotor') having an inner diameter which may be suitable for applications such as CT scanning, of, for example, 0.5 to 2 meters, that is adapted to rotate around a central axis. The illustrated rotor bearing 102, which may be implemented as an integral molded or cast steel component, includes raceways 104, 106 for seating ball bearings, and a plurality of alternating protruding and receding sections, e.g., 108 position circumferentially around the outer surface, of which the protruding sections are referred to as "teeth". In other embodiments, discussed further below, the teeth are not an integral part of the rotor, but rather, may be implemented as laminated sections of steel that are mountable onto a the section of the bearing 102 shown. The number and spacing of the teeth are set in accordance with the design of the stator section 110 of the motor.

The stator 110 is arranged to surround and circumscribe at least a part of the outer surface of the rotor with a small air gap (e.g., <1 cm.) in between. Preferably, the stator arc subtends considerably less than 360 degrees, for example, 90 to 270 degrees, or even less than 90 degrees. In some embodiments, multiple stators can also be used; for example, two stators, with each stator subtending 150 degrees may be used. However, as the torque provided by the motor 100 is proportional to the arc length of the stator, some applications may require smaller or larger arc lengths, and the present invention contemplates implementations of any stator arc length up to 360 degrees.

The stator 110 includes a set of permanent magnets, e.g., 112 arranged along the arc length of the stator, which may be embedded in a housing. The permanent magnets are preferably made of rare earth magnetic materials but may be made from other magnetic materials as well. A set of conductive coils, e.g., 114, is arranged around the stator laminations. In flux-switch motors, the permanent magnets, e.g., 112, are arranged with alternating polarities which produce a first magnetic flux pattern, referred to as "field flux". In addition, an alternating current is applied the coils, e.g., 114, which, in turn, generate a second magnetic flux pattern referred to as the "armature flux". In operation, the magnetic flux lines generated by the interaction of the field and armature flux seek to close through the magnetic material of the teeth of the rotor, which thereby generates torque on the rotor.

Figure 2:
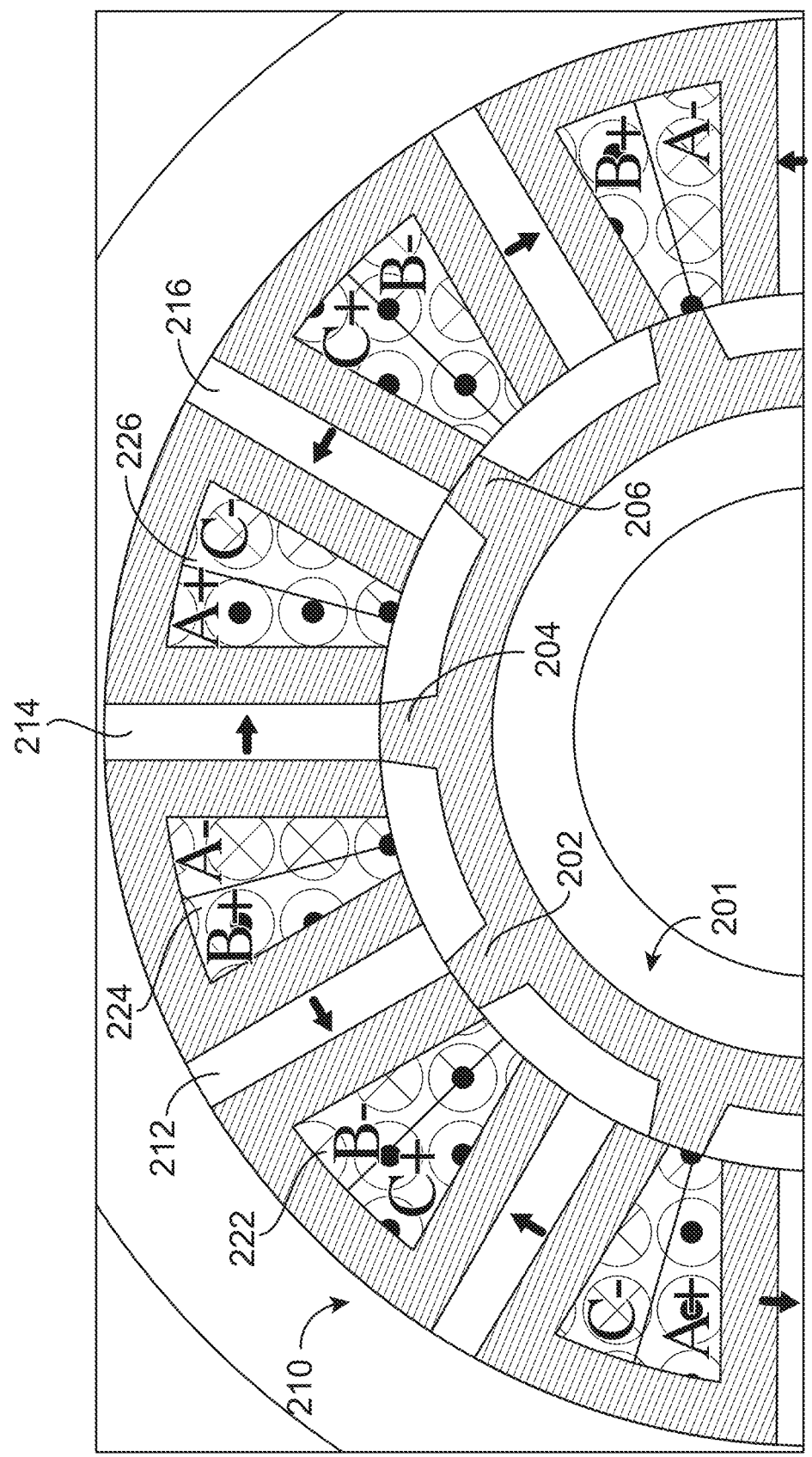
FIG. 2 is a schematic cross-sectional view of a flux-switch motor according to an embodiment of the present invention.

FIG. 2 is a schematic cross-sectional view of an exemplary flux-switch motor illustrating the staggered relationship between the teeth of the rotor and the permanent magnets of the stator. The rotor 201, including teeth, e.g., 202, 204, 206, is positioned beneath the stator 210, which includes permanent magnets, e.g., 212, 214, 216, and coil sections, e.g., 222, 224, 226 positioned between the permanent magnet sections. The permanent magnets 212, 214, 216 and coils are embedded in a backiron housing, which may comprise laminated steel sections.

As shown in the figure, the permanent magnet areas 212, 214, 216 on the stator are positioned more closely together than the teeth 202, 204, 206 of the rotor, so that adjacent teeth cannot align with adjacent permanent magnets. For example, as shown in FIG. 2, rotor tooth 204 is aligned with permanent magnet 214, but teeth 202, 206 are not aligned with respective permanent magnets 212, 216. In this manner the teeth and magnets are said to be staggered with respect to each other. This staggered relationship aids in generating torque in the rotor as shown more clearly with reference to FIGS. 3A and 3B. However, in other embodiments, the rotor teeth may be positioned more closely together than the stator permanent magnet sections, in which case the staggering is reversed.

Figure 3A:
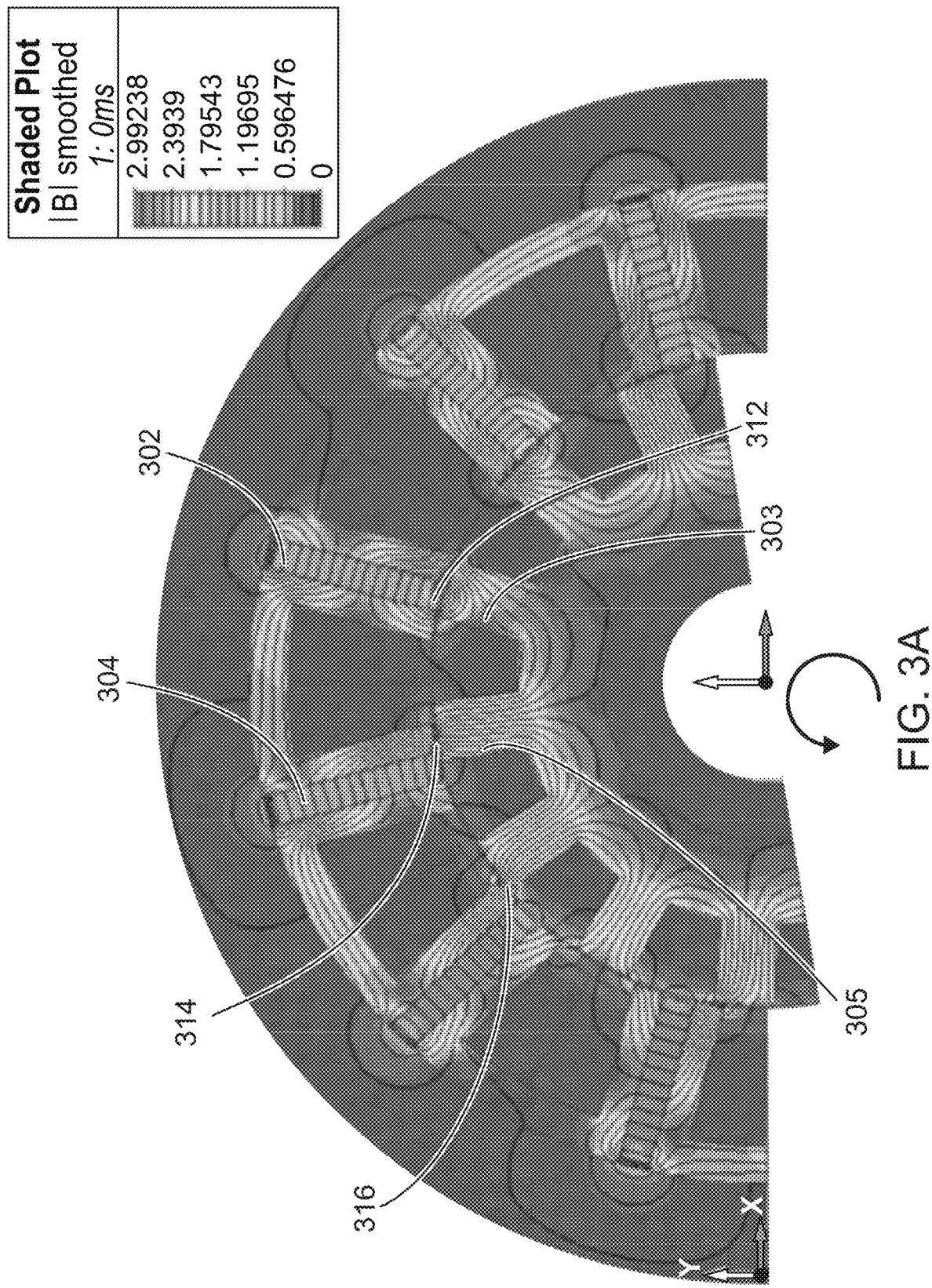
FIG. 3A is a schematic cross-sectional view of a flux-switch motor in an example starting position showing magnetic flux lines generated in the motor.

FIG. 3A is another schematic cross-sectional view of a flux-switch motor in an example starting position showing magnetic flux lines generated in the motor. The permanent magnet sections, e.g., 302 in this example comprise magnetic sections, polarized in the horizontal direction. The flux lines shown emerging from the poles of the individual sections seek to close or end at a pole of the opposite polarity. The proximity of the rotor, made of magnetic material affects the distribution of flow of the magnetic flux lines, which in turn produces variation of magnetic forces on the rotor. As shown in the figure, rotor tooth 303 is approximately aligned with permanent magnet 302, and in this area 316 the magnetic flux lines from the permanent magnet close and reach the other side of the magnet through the material of rotor tooth 303. However, in the airgap region 314 between the left-adjacent permanent magnet 304 and rotor tooth 305, in which rotor tooth 305 is positioned to the right of alignment with permanent magnet 304, the flux lines are not able to close through the rotor tooth, but rather, become compressed, increasing the magnetic flux density in region 314. The change in relative magnetic flux density generates a force on the rotor to move the rotor tooth 305 leftward into alignment with magnet 304. Similar forces act in the region 316 on the next adjacent rotor tooth exerting a force both leftward and downward. Together, the forces exert a counterclockwise torque on the rotor. The length of the stator arc and all the particular geometries and materials of the component parts, such as magnets, steel laminations, windings, rotor features, etc., are configured to provide specific rotor torques and speeds for any given application.

Figure 3B:
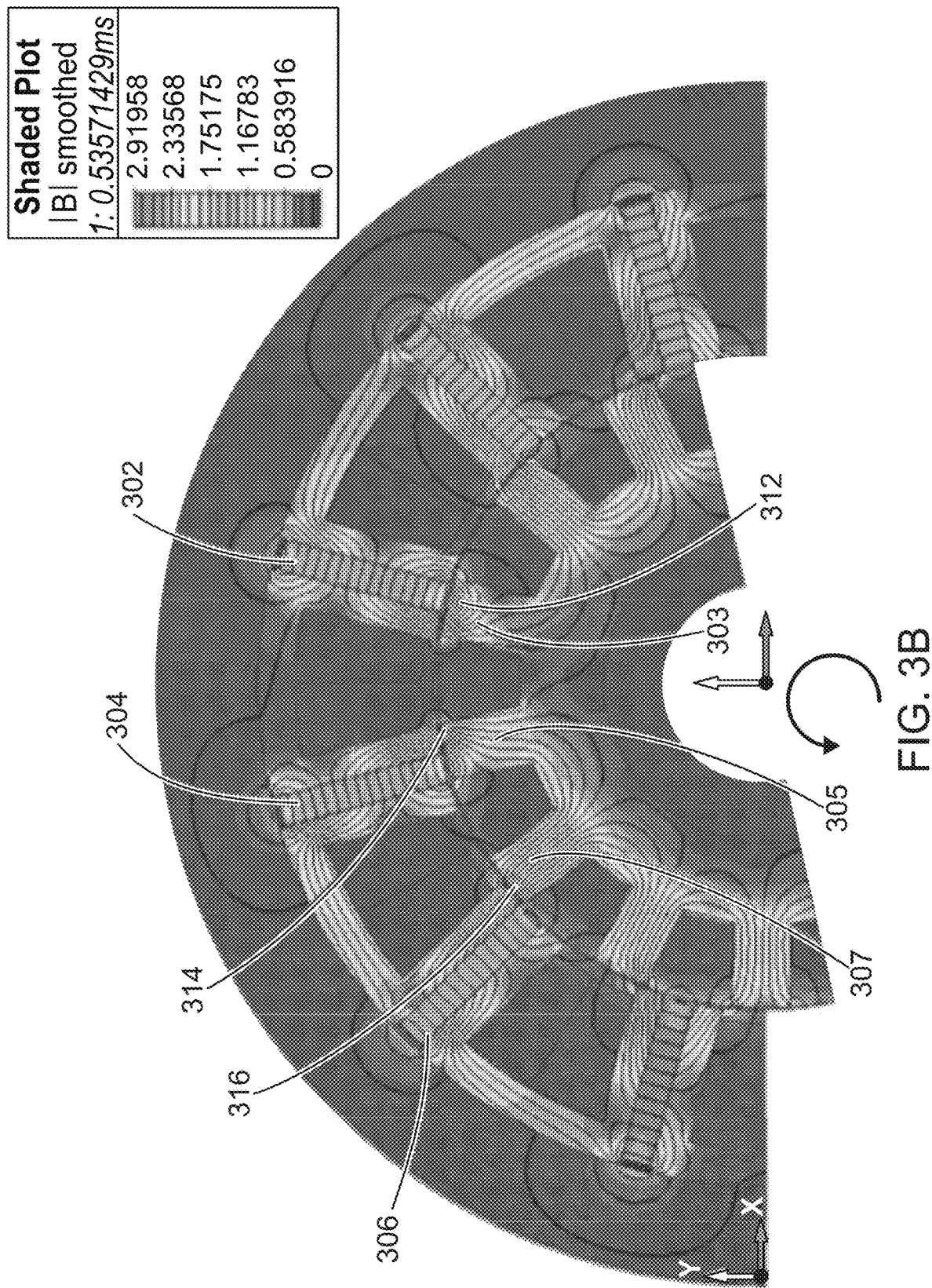
FIG. 3B shows the same schematic view as shown in FIG. 3A in a subsequent position after a rotation of the rotor.

FIG. 3B shows the same view as FIG. 3A later in time with the rotor having rotated counterclockwise by several degrees. As shown, the torque acting on the rotor teeth has pulled rotor tooth 305 closer in alignment with permanent magnet 304, and the flux lines in region 314 are beginning to close through rotor tooth 305. The flux density in region 316 has increased in comparison with FIG. 3A, increasing the forces in that region acting to bring rotor tooth 307 into alignment with permanent magnet 306. Meanwhile, the rotational motion of the rotor has moved rotor tooth 303 out of alignment with permanent magnet 301.

Figure 4:
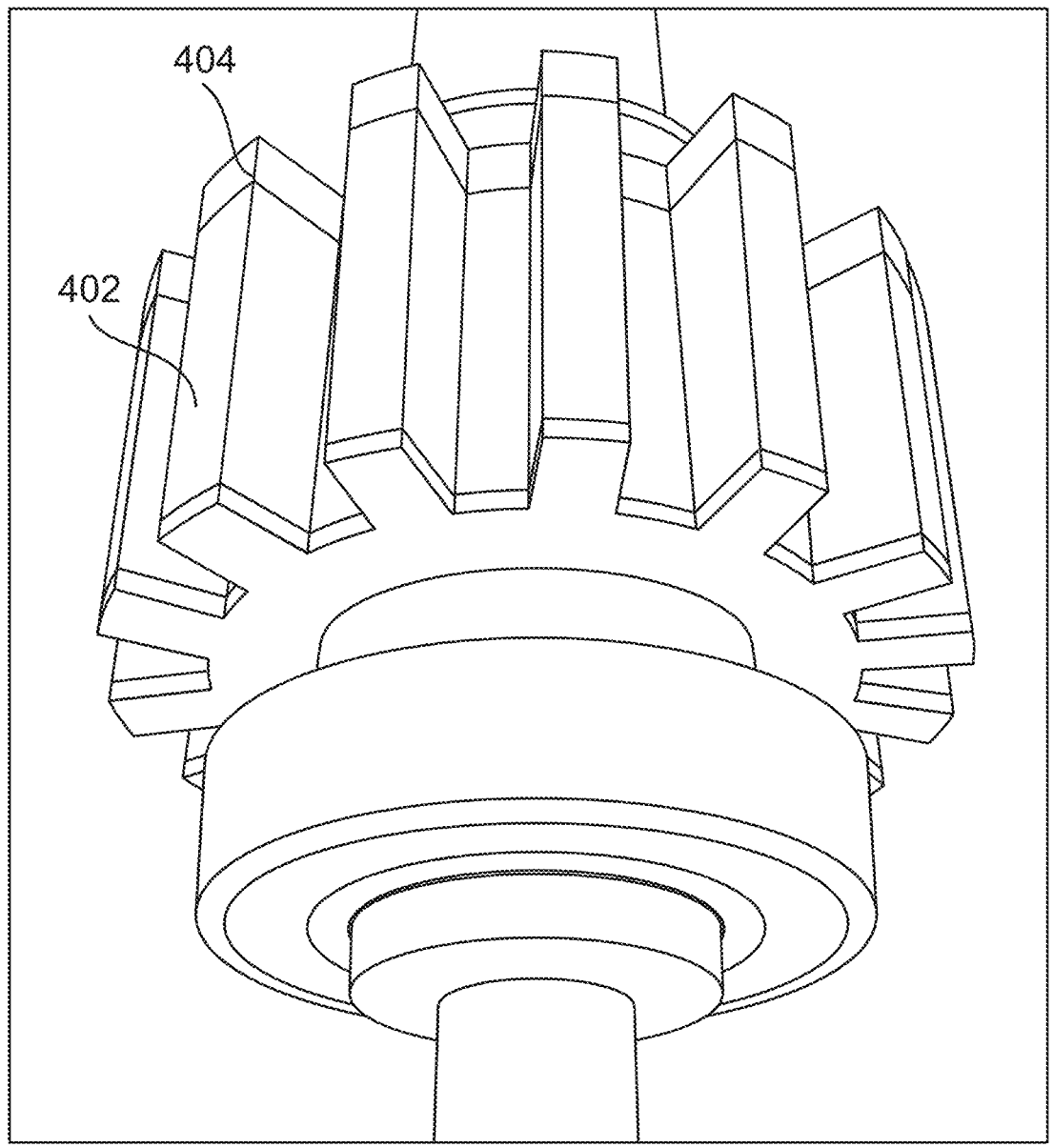
FIG. 4 is top perspective view showing an exemplary set of laminated rotor teeth according to an embodiment of the present invention.
Figure 6:
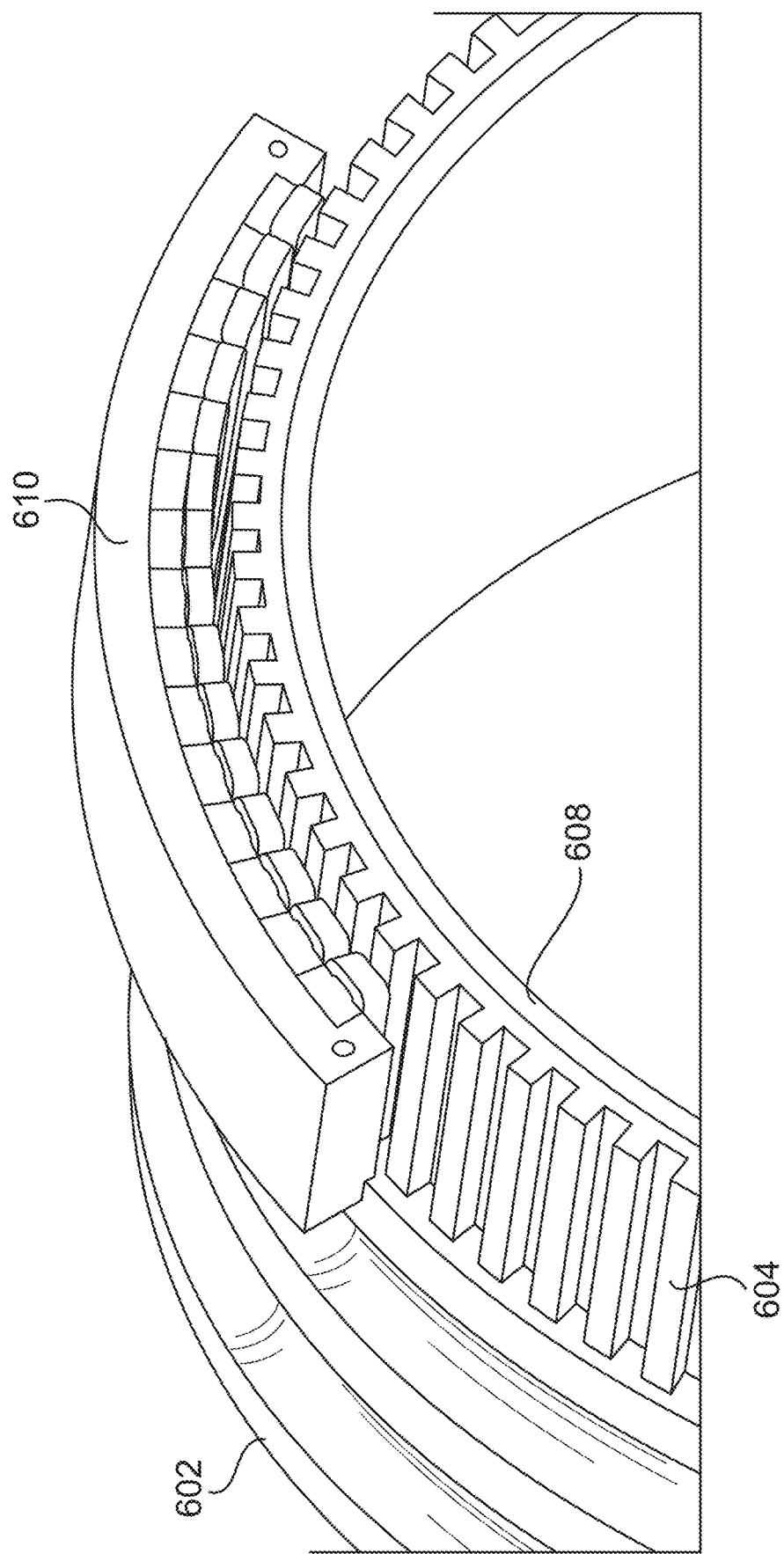
FIG. 6 is a perspective view of a section of a rotary motor according to an alternative embodiment of the present invention.

It is noted that one of the benefits of a flux-switch topology is that all of the components for generating magnetic flux are located in the fixed stator, allowing the design of the rotor to be dramatically simplified. As noted, the length of stator arc and all the particular geometries and materials of the component parts, such as magnets, steel laminations, windings, rotor features, etc., are optimized for any given use case or application. For example, the rotor teeth portion that participates in the magnetic circuit may be laminated depending on the particular application. FIG. 4 is a top perspective view of an exemplary rotor section including laminated teeth. As can be discerned, each tooth is composed of a stack of thin laminated steel sections, e.g., 402, 404 arranged in the axial direction. As noted above, in some embodiments the laminated rotor teeth may not be integrated with the rotor bearing component, but rather, may be mountable onto a surface of the motor bearing adapted to receive the rotor teeth. FIG. 6 shows an alternate embodiment of the rotary motor shown in FIG. 1 in which separate rotor teeth 604 have been inserted and mounted on receiving surface 608 of the rotor bearing 602. The receiving surface is positioned directly under the stator 610 to enable interaction between the rotor teeth 604 and the stator elements.

Although flux-switched topologies have the advantages of simpler rotor structure, in that the rotor does not need to include any permanent magnetic material, flux-switch topologies are subject to high temperatures in the eddy current losses in the steel sections of the stator or rotor. These drawbacks are lessened to a large extent by lamination of the interactive rotor section as shown in FIG. 4.

In CT scanning applications air flow is typically maintained in the apparatus during examinations. As the airflow may pass proximally to the windings and magnets of the stator, it may have a sufficient cooling effect to counteract the heating of the stator elements during operation. Air flow and/or other cooling methods may also be used in a variety of other 'large diameter' applications where the large diameter of the rotor bearing provides sufficient space for air flow.

It will be understood by those of ordinary skill in the art that various changes may be made and equivalents may be substituted for element without departing form the scope of the invention. In addition, many modifications may be made to adapt a particular feature of material to the teachings of the invention without departing from the scope thereof. Therefore, it is intended that the invention not be limited to the particular embodiments disclosed, but that the invention will include all embodiments falling within the scope of the claims.

What is claimed is:

1. A rotary motor comprising:

an annular rotatable bearing having an inner surface and an outer surface, the bearing including a rotatable bearing surface and a plurality of magnetic rotor teeth elements positioned around a circumference of the outer surface of the rotatable bearing, wherein the rotatable bearing and the rotor teeth elements are formed integrally as a single rotor unit; and one or more stators, the one or more stators having a total arc length of less than 360 degrees, and each including a plurality of permanent magnets and a plurality of energizable coils, each of the one or more stators mounted separately from and positioned with respect to the bearing such that the plurality of rotor teeth elements of the bearing are radially proximate to the permanent magnets of the one or more stators to enable interaction between the rotor teeth and the one or more stators; and wherein upon application of alternating current in a flux switch pattern in the plurality of energizable coils of the one or more stators, torque is applied to the plurality of magnetic rotor teeth elements.

2. The rotary motor of claim 1, wherein the annular bearing includes at least one raceway on the outer surface to receive ball bearings.

3. The rotary motor of claim 1, wherein the rotor teeth elements include laminated layers.

4. The rotary motor of claim 1, wherein the inner surface of the annular bearing has a diameter equal to or greater than 0.5 meters.

* * * * *